(12) United States Patent
Guan et al.

(10) Patent No.: US 6,617,116 B2
(45) Date of Patent: *Sep. 9, 2003

(54) ASSAY DEVICES AND METHODS OF ANALYTE DETECTION

(75) Inventors: Ming Guan, Singapore (SG); Hsiao Ying Chen, Singapore (SG)

(73) Assignee: Genelabs Diagnostics Pte. Ltd., Singapore Science Park (SG)

( * ) Notice: Subject to any disclaimer, the term of this patent is extended or adjusted under 35 U.S.C. 154(b) by 0 days.

This patent is subject to a terminal disclaimer.

(21) Appl. No.: 09/771,479

(22) Filed: Jan. 25, 2001

(65) Prior Publication Data

US 2001/0023076 A1 Sep. 20, 2001

Related U.S. Application Data

(63) Continuation-in-part of application No. 09/493,408, filed on Jan. 28, 2000, now Pat. No. 6,316,205.

(51) Int. Cl.⁷ .................. C12M 1/34; G01N 21/00; G01N 33/53; G01N 33/543
(52) U.S. Cl. .................. 435/7.1; 435/4; 435/7.4; 435/7.92; 435/7.93; 435/7.94; 435/287.1; 435/287.2; 435/287.9; 435/810; 435/970; 436/164; 436/169; 436/514; 436/518; 436/524; 436/528; 436/530; 436/810; 422/55; 422/58; 422/61; 422/68.1
(58) Field of Search ................ 422/55, 58, 61, 422/68.1; 435/4, 7.4, 7.1, 7.92, 7.93, 7.94, 287.1, 287.2, 287.9, 810, 970; 436/164, 169, 514, 530, 810, 518, 524, 528

(56) References Cited

U.S. PATENT DOCUMENTS

| 4,575,484 A | * | 3/1986 | Straus ............... 435/7.32 |
| 4,790,979 A | | 12/1988 | Terminiello et al. |
| 4,933,092 A | | 6/1990 | Aunet et al. |
| 5,354,692 A | | 10/1994 | Yang et al. |
| 5,452,716 A | | 9/1995 | Clift |

(List continued on next page.)

FOREIGN PATENT DOCUMENTS

| EP | 0 262 328 A2 | 4/1988 |
| WO | WO 97/09428 A2 | 3/1997 |
| WO | WO 97/09429 A2 | 3/1997 |
| WO | WO 97/21103 A1 | 6/1997 |
| WO | WO 97/28264 A1 | 8/1997 |

(List continued on next page.)

OTHER PUBLICATIONS

Andersen et al. (1995) "Recall of Long–Lived Immunity to Mycobacterium tuberculosis Infection in Mice." J. Immunol. 154:3359–3372.

(List continued on next page.)

Primary Examiner—Long V. Le
Assistant Examiner—Kartic Padmanabhan
(74) Attorney, Agent, or Firm—Junrui Yang; Angela P. Horne; Quine Intellectual Property Law Group, P.C.

(57) ABSTRACT

Assay devices, kits, and methods for detection of one or more analytes in a sample are provided. The assay device features the controlled release of reagents and hence is particularly suitable for binding assays such as immunoassays. The assay device achieves greater sensitivity than conventional rapid test assays, leading to stronger and/or more stable visual signals than those produced by conventional devices, easier interpretation of results, and reduced occurrence of indeterminate results. The device can be used for detecting analyte in a variety of biological samples without the need for conventional sample filtration techniques, and thus is suitable for use by untrained personnel without specialized equipment. In addition, the device can be used to simultaneously analyze a number of analytes using a single sample.

5 Claims, 5 Drawing Sheets

U.S. PATENT DOCUMENTS

| | | | | |
|---|---|---|---|---|
| 5,494,799 | A | * 2/1996 | Wood et al. | 435/7.32 |
| 5,607,863 | A | 3/1997 | Chandler | |
| 5,665,238 | A | 9/1997 | Whitson et al. | |
| 5,753,517 | A | 5/1998 | Brooks et al. | |
| 5,776,723 | A | * 7/1998 | Herold et al. | 435/34 |
| 6,316,205 | B1 | * 11/2001 | Guan et al. | 435/7.1 |
| 6,379,902 | B1 | * 4/2002 | Laqueyrerie et al. | 435/7.1 |
| 6,383,763 | B1 | * 5/2002 | Wallis | 435/7.32 |

FOREIGN PATENT DOCUMENTS

| | | |
|---|---|---|
| WO | WO 97/44463 A2 | 11/1997 |
| WO | WO 98/07847 A1 | 2/1998 |
| WO | WO 98/12562 A1 | 3/1998 |
| WO | WO 98/16645 A2 | 4/1998 |
| WO | WO 98/16646 A3 | 4/1998 |
| WO | WO 98/27432 A1 | 6/1998 |
| WO | WO 98/30699 A1 | 7/1998 |
| WO | WO 98/32768 A1 | 7/1998 |
| WO | WO 98/32862 A2 | 7/1998 |
| WO | WO 98/36089 A3 | 8/1998 |
| WO | WO 98/41533 A1 | 9/1998 |
| WO | WO 98/49314 A3 | 11/1998 |
| WO | WO 98/53075 A2 | 11/1998 |
| WO | WO 98/53076 A2 | 11/1998 |
| WO | WO 98/56815 A1 | 12/1998 |
| WO | WO 99/42118 A2 | 8/1999 |
| WO | WO 99/48919 A1 | 9/1999 |
| WO | WO 99/51748 A2 | 10/1999 |
| WO | WO 00/55194 A3 | 9/2000 |

OTHER PUBLICATIONS

Andersen et al. (2000) "Specific immune–based diagnosis of tuberculosis." *Lancet* 356:1099–1104.

Anderson and Hansen (1989) "Structure and Mapping of Antigenic Domains of Protein Antigen b, a 38,000–Molecular–Weight Protein of *Mycobacterium tuberculosis*." *Infect. Immun.* 57:2481–2488.

Cocito and Vanlinden (1986) "Preparation and properties of antigen 60 from *Mycobacterium bovis* BCG." *Clin. Exp. Immunol.* 66:262–272.

Coler et al. (2000) "Colning of a *Mycobacterium tuberculosis* Gene Encoding a Purified Protein Derivative Protein That Elicits Strong Tuberculosis–Specific Delayed–Type Hypersensitivity." *J. Infectious Diseases* 182:224–233.

Daley et al. (1992) "An Outbreak of Tuberculosis with Accelerated Progression Among Persons Infected with the Human Immunodeficiency Virus." *New Engl. J Med.* 23;326(4):231–235.

Desem and Jones (1998) "Development of a Human Gamma Interferon Enzyme Immunoassay and Comparison with Tuberculin Skin Testing ofor Detection of *Mycobacterium tuberculosis* Infection." *Clin. Diag. Lab. Immunol.* 5:531–536.

Dillon et al., (2000) "Molecular and Immunological Characterization of *Mycobacterium tuberculosis* CFP–10, an Immunodiagnostic Antigen Missing in *Mycobacterium bois* BCG." *J. Clin. Microbiology* 38:3285–3290.

Enroth et al. (1997) "Diagnostic Accuracy of a Rapid Whole–Blood Test for Detection of *Helicobacter pylori.*" *J. Clin. Micro.* 35: 2695–97.

Freeman et al (1999) "Rapid Immunochromatographic Assay for Diagnosis of Tuberculosis Antibodies Detected May Not Be Specific." *J. Clin. Microbiol.* 37(6):2111–2112.

Giles et al. (1999) "Simple/Rapid Test Devices for Anti–HIV Screening: Do they Come Up to the Mark?." *Journal of Medical Virology* 59:104–109.

Hackelsberger et al. (1998) "Performance of a Rapid Whole Blood Test for *Helicobacter pylori* in Primary Care: A German Multicenter Study." *Helicobacter* 3: 179–183.

Harboe et al. (1986) "Properties of Proteins MPB64, MPB70, and MPB80 of *Mycobacterium bovis.*" *Infect. Immun.* 52:293–302.

Havlir and Barnes (1999) "Tuberculosis in Patents with Human Immunodefiency Virus Infection." *New Engl. J Med.* 4;340(5):367–373.

Henrickson et al., (2000) "Mass Spectrometric Identification of Mtb81, a Novel Serological Marker for Tuberculosis." *J. Clin. Microbiology* 38:2354–2361.

Huang et al. (1998) "Meta–analysis of the Relationship Between *Helicobacter pylori* Seropositivity and Gastric Cancer." *Gasteroenterology* 114: 1169–79.

Hunter et al., (1986) "Structure and Antigenicity of the Phosphorylated Lipopolysaccharide Antigens from the Lepros and Tubercle Bacilli." *J. Biol. Chem.* 261:12345–12351.

Leung et al. (1998) "Comparison of Two Rapid Whole–Blood Tests for *Helicobacter pylori* Infection in Chinese Patients." *J. Clin. Micro.* 36:3441–3442.

Periera et al (2000) "Development of Antigen Detection Assay for Diagonosis of Tuberculosis Using Sputum Samples." *J. Clin. Microbiol.* 38:2278–2283.

Perkins (2000) "New diagnostic tools for tuberculosis." *Int. J. Tuberc. Lung Dis.* 4(12):51–57.

Pottumarthy et al. (1999) "Evaluation of the Tuberculin Gamma Interferon Assay: Potential To Replace the Mantoux Skin Test." *J. Clin. Microbiol.* 37(10):3229–3232.

Pottumarthy et al. (2000) "A Comparison of Seven Tests for Serological Diagnosis of Tuberculosis." J. Clin. Microbiol. 38(6):2227–2231.

Rasolofo and Chanteau (1999) "Field Evaluation of Rapid Tests for Tuberculosis Diagnosis." *J. Clin. Microbiol.* 37(12):4201.

Salata et al. (1991) "Purification and Characterization of the 30,000 dalton native antigen of *Mycobacterium tuberculosis* and characterization of six monoclonal antibodies reactive with a major epitope of this antigen." *J. Lab. Clin. Med.* 118:589–598.

Schaaf et al. (1996) "The 5–yean outcome of multidrug resistant tuberculosis patients in the Cape Province of South Africa." Trop Med. Int. Health Oct.;1(5):718–722.

Selwyn et al. (1989) "A Prospective Study of the Risk of Tuberculosis Among Intravenous Drug Users with Human Immunodefiency Virus Infection." *New Engl. J Med.* 2;320(9):545–550.

Stone et al. (1997) "Near patient testing for *Helicobacter pylori*: a detailed evaluation of the Cortecs Helisal Rapid Blood test." *Eur. J. of Gastroenterol. & Hepatology* 9: 257–260.

Verbon et al. (1992) "Characterization of B cells epitopes on the 16K antigen of *Mycobacterium tuberculosis.*" *Clin. Exp. Immunol.* 89:395–401.

* cited by examiner

ASSAY DEVICES AND METHODS OF ANALYTE DETECTION

CROSS-REFERENCES TO RELATED APPLICATIONS

This application claims priority to and benefit of U.S. application Ser. No. 09/493,408, filed Jan. 28, 2000, now U.S. Pat. No. 6,316,205, the full disclosure of which is incorporated herein by reference.

BACKGROUND OF THE INVENTION

Chromatographic assay systems employed as rapid assay devices are one of several means for detecting the presence of a given analyte in a biological sample. One advantage to these systems is that the execution of these assays does not use additional specialized equipment or trained personnel. Another advantage is the great variety of analytes that can be detected using this type of assay. The use of rapid chromatographic techniques for detection of the presence of an analyte in a biological sample has thus progressed beyond the bounds of the clinical laboratory, as assay devices employing these techniques have been found to be especially valuable in "point of care" situations such as the doctor's office or home settings.

The typical rapid chromatographic tests utilize either a "sandwich" assay or a "competition" assay to detect the presence of a desired analyte. In the sandwich assay, an analyte is bound, or "sandwiched," between an unlabeled first binding partner and a labeled second binding partner. For example, an analyte, such as an antibody to HIV, can be captured by a first binding partner, in this case, an HIV antigen immobilized on a membrane. The antibody-antigen complex can then be detected by a second binding partner having a label, such as another HIV antigen tagged with a colored particle.

In contrast, during the competition assay, the analyte in the sample competes with a labeled analyte, or labeled analogue to the analyte, for a binding partner immobilized on a solid support. A greater concentration of analyte in the sample results in a lower signal in the assay, as the labeled analytes are competed away from the binding partner on the solid support (i.e., the signal produced during a competition assay decreases as the concentration of analyte in the sample increases). Thus, the sandwich assay provides a qualitative assessment with great sensitivity, while the competition assay provides a quantitative measure of analyte concentration.

Regardless of the analyte-detecting method used, the rapid assay devices currently available are often categorized into one of three basic formats: the "dipstick" format, the "flow through" format, and the "lateral flow" format. The "dipstick" format (exemplified in U.S. Pat. Nos. 5,275,785, 5,504,013, 5,602,040, 5,622,871 and 5,656,503) typically consists of a strip of porous material having a sample receiving end, a reagent zone and a reaction zone. The sample is wicked along the assay device starting at the sample-receiving end and moving into the reagent zone. The analyte to be detected binds to a reagent incorporated into the reagent zone, preferably a labeled binding partner, to form a complex. Typically, these binding pairs are antibody-:antigen complexes, or a receptor:ligand complexes having a label such as a colloidal metal incorporated into the reagent portion of the complex. The labeled binding partner-antigen complex then migrates into the reaction zone, where the complex is captured by another specific binding partner firmly immobilized in the reaction zone. Retention of the labeled complex within the reaction zone thus results in a visible readout.

The "flow through" format (U.S. Pat. No. 4,020,046) also utilizes porous solid phase materials. This assay format usually has a porous membrane that contains an immobilized binding partner positioned above an absorptive layer. Once the sample has been added to the membrane surface, the analyte of interest reacts with the immobilized binding partner to form an analyte-binding partner complex. The complex is visualized by addition of a second binding partner having a label, such as an enzyme, one or more dye particles or various colloidal metals. The absorptive layer acts as a sink for excess assay reagents, and can be used to regulate the flow rate of the reactants to achieve optimal reaction between the analyte and the binding partner. In this format, the sensitivity of the readout can be improved by "washing" the membrane with additional solution to reduce any nonspecific binding of the label, or to remove any other materials which can interfere with the assay readout.

The "lateral flow" format (see U.S. Pat. Nos. 5,075,078, 5,096,837, 5,354,692 and 5,229,073) utilizes a porous solid phase material and has a linear construction similar to that of the dipstick assay format: a sample application site, a reagent releasing site and a reaction site. However, instead of vertically wicking the samples up the "dipstick," the lateral flow format allows a sample to flow laterally across the porous solid phase material. The sample is applied directly to the application site and the analyte of interest flows laterally to the reagent-releasing site, and forms a complex with a labeled binding partner. The analyte:binding partner complex then migrates into the reaction site where it is captured by a second, immobilized binding partner and detected.

The conventional rapid assays are a popular choice for determining the presence of a given analyte in samples provided at the "point of care" sites because they are relatively easy to use, do not use specialized equipment or personnel, and produce results in a short amount of time. For example, simple and rapid immunoassay devices for infectious diseases such as AIDS have been available for almost a decade. However, the existing rapid tests are not without their shortcomings. Most importantly, the sensitivity of such devices has often been questioned, due to various limitations with the currently available formats (Giles et al. (1999) *Journal of Medical Virology* 59:104–109). In addition, there are several practical limitations to the use of these assay devices inherent in the design of the assay format, as exemplified below.

The dipstick format, which was originally designed for urine analysis, uses a relatively large volume of sample for analysis. This is a considerable limitation to use of such a device for analysis of serum or blood samples. In contrast, assay devices based on the flow-through format reduce the volume requirement of samples significantly. However, the flow-through format cannot be employed in a truly self-contained device. In devices based on the flow-through format, the detecting reagent (i.e. the labeled binding partner) is not directly incorporated into the porous solid matrix of device and thus must be provided separately. This leads to additional limitations regarding reagent stability, if the detecting reagents are provided in liquid form, or issues surrounding the proper preparation and handling of the detecting reagent, if provided in a dried form.

The lateral flow format overcomes both the sample volume problem of the dipstick format, as well as the detecting reagent issue of the flow-through format. However, the lateral-flow format does not allow for a washing step, as inherent in the flow-through format. Any interfering species, such as particulate or colored material introduced by the sample solution, or unbound label, can potentially interfere with the readout of the assay device. As a result, the lateral flow format often employs filtration during the assay procedure, e.g., using specially coated filters to remove potential interfering species prior to detection of the analyte. (see, for example, U.S. Pat. Nos. 4,933,092, 5,452,716, and 5,665,238)

A number of clinical conditions are (or could be) monitored using one or more rapid assay devices. For example, *Helicobacter pylori* has been identified as a pathogen leading to chronic gastritis, peptic ulcer, gastric cancer and mucosa-associated lymphoid tissue (MALT) lymphoma (Huang et al. (1998) Gasteroenterology 114:1169–79). The conventional "gold standard" tests typically involve invasive endoscopy, followed by histology, culture or rapid urease tests, all of which necessitate a hospital laboratory setting and specially trained medical personnel. On the other hand, the near-patient whole blood or serum/plasma based rapid test devices that have recently become available have not lived up to expectations. There are mixed reports regarding the performances of these kits, particularly in correlation to the ethnic profile of sera being examined. Although some of these rapid test kits perform with approximately 90% sensitivity, often these same kits are compromised by lower performances in specificities, especially when used in different geographical territories. The reverse is also true of kits with high specificities but low sensitivities (see Enroth et al. (1997) J. Cling. Micro. 35:2695–97; Stone et al. (1997) Eur. J. of Gastroenterol. & Hepatology 9:257–260; Hackelsberger et al. (1998) Helicobacter 3:179–183; Leung et al. (1998) J. Clin. Micro. 36:3441–3442). For example, when used to test Asian populations, kits developed using Western serum panels were found to have poorer performance profiles ranging from 63–84% in sensitivity and 82–84% in specificity, considerably lower than those recorded for Western serum panels (Leung, supra). There is an obvious need for an accurate rapid test device for global use, that is both sensitive and specific without compromising one feature for the other.

Tuberculosis (TB) is another example of a clinical condition that would benefit from an improved rapid assay device (for a review of current diagnostic tests, see Andersen et al. (2000) Lancet 356:1099–1104). The re-emerging of this chronic disease is believed to be due largely to the emergence of drug-resistant strains of *M. tuberculosis*, in concert with a demonstrated increase in risk of infection among human immunodeficiency virus (HIV)-infected populations (for reviews, see Daley et al. (1992) New Engl. J Med. 23;326(4):231–235; Havlir and Barnes (1999) New Engl. J Med. 4;340(5):367–373; Schaaf et al. (1996) Trop Med. Int. Health Oct;1(5):718–722; and Selwyn et al. (1989) New Engl. J Med. 2;320(9):545–550). Acid-fast bacilli (AFB) microscopy employing a Ziehl-Neelson staining protocol is currently the primary diagnostic and monitoring technique, despite the inherent lack of sensitivity and stringent assay requirements (Perkins (2000) Int. J. Tuberc. Lung Dis. 4(12):51–57; Periera et al (2000) J. Clin. Microbiol. 38:2278–2283). On the other hand, the usefulness of currently available serological tests is debated (Freeman et al (1999) J. Clin. Microbiol. 37(6):2111–2112; Rasolofo and Chanteau (1999) J. Clin. Microbiol. 37(12):4201; Desem and Jones (1998) Clin. Diag. Lab. Immunol. 5:531–536). A recent evaluation of seven currently available serological tests revealed that the sensitivities of such tests are lower than previously reported (Pottumarthy et al. (2000) J. Clin. Microbiol. 38(6):2227–31). Furthermore, the sensitivities of standard serological tests are often heavily diminished in tuberculosis patients co-infected with HIV. There is still an unmet need for new rapid assay devices, particularly those that provide a rapid, inexpensive and accurate test for the diagnosis of TB.

SUMMARY OF THE INVENTION

The present invention provides novel assay devices, test kits, and methods for detecting the presence of one or more analytes in a sample. The novel approach of the present invention provides optimal control of the assay reactions without requiring specially-developed specific antibodies, large volumes of sample, or complicated arrays of reagents or fluid pathways (for example, as compared to that described in U.S. Pat. Nos. 4,960,691 and 5,607,863). The present invention presents assay devices that are particularly suitable for rapid chromatographic assays using a controlled series of reactions. By controlling the release of the different reagents used in the assay device, the sensitivity of the assay is improved as compared to conventional assays, without compromising the specificity of the assay. The assay devices use a small volume of sample and achieve a much higher titration-end-point activity than conventional lateral flow assays. In addition, the assay devices of the present invention provide better assay sensitivity, without compromising specificity, a highly desirable improvement in the field of rapid chromatographic detection. In addition, the assay can be performed by untrained personnel in a minimum amount of time, and without the need for specialized equipment.

Accordingly, the present invention provides assay devices for use in detecting the presence of an analyte. One embodiment of the assay device of the present invention includes (a) a chromatographic element comprising a sample receiving end, a reagent releasing end, and a reaction zone; (b) an absorbent pad; and (c) a separator positioned between the chromatographic element and the absorbent pad. The separator employed in the present device includes, but is not limited to, a fluid-impermeable barrier, semi-permeable membrane, a material which dissolves over time upon exposure to an aqueous solution, and the like. Using an assay device of this first embodiment, a sample is applied to the sample-receiving end of the chromatographic element and allowed to migrate laterally by capillary action towards the reagent-releasing end. After the sample covers the reaction zone and the analyte within the sample has interacted with at least one first binding partner immobilized within the reaction zone, an aqueous solution is added to the reagent releasing end of the chromatographic element. The separator is removed (or partially removed) from the device, allowing the absorbent pad to come into contact with the chromatographic element. The aqueous solution can be added prior to the removal of the separator, concurrently with the removal, or immediately afterwards. The separator can be removed by pulling the separator entirely from the assay device, or it can be partially removed such that the sample receiving end of the chromatographic element and the absorbent pad come into contact. One or more reagents embedded at the reagent-releasing end, such as a second binding partner labeled with a detectable label such as a naturally colored particle, are released by addition of the aqueous solution and moved toward the reaction zone by the pulling force of the absorber pad. Thus, the device according to this embodiment allows the analyte to form a complex with the first binding partner prior to the reaction between the labeled second binding partner and the bound analyte complex. In addition, the aqueous solution added to the reagent releasing end of the chromatographic element acts not only as a reagent releasing solvent but also as a wash liquid. As a result, a visual readout with a clear background is observed within the reaction zone.

Another embodiment of the assay devices of the present invention includes (a) a chromatographic element comprising a sample receiving end having a releasable first binding partner, a reaction zone having an immobilized second binding partner, and a reagent releasing end having a releasable third binding partner containing a label; (b) an absorbent pad; and (c) a separator positioned between the chromatographic element and the absorbent pad. This embodiment of the assay device is preferred when a capture assay is desired. Using an assay device of this second embodiment, the analyte (for example, an antibody) reacts with at least one first binding partner (such as an antigen or a recombinant protein) impregnated at the sample receiving end of the chromatographic element. The analyte-binding partner complex then migrates to the reaction zone, where this first complex is captured by an immobilized second binding partner (the "capturing reagent", such as anti-human IgG or anti-human IgM antibodies) to form a second complex. When the aqueous solution is added and the separator is removed, one or more third binding partners labeled with a detectable label, such as a naturally colored particle, are released from the reagent releasing end of the chromatographic element, and allowed to laterally flow to the reaction zone. Detectable labels include moieties which can be detected by visual inspection (e.g., moieties which include or produce colored elements), or with the aid of artificial detection systems, including. e.g., optical systems, spectroscopic systems, radiographic systems, or the like. For simplicity of operation, visually detectable labels are preferred.

The third binding partner can interact with the second complex to form a third complex, which can be detected via the label incorporated in the third binding partner. Optionally, the first binding partner is single antigen or a mixture of antigens, and a generic reagent is used as the third labeled binding partner. For example, the generic reagent optionally is an anti-GST antibody, which will react with all GST-constructed recombinant antigens.

Similarly, a third embodiment of the present invention encompasses the use of two or more reagents interacting at the reagent releasing end of a chromatographic element prior to migration across the reaction zone. In this embodiment of the present invention, the assay devices comprise (a) a chromatographic element comprising a sample receiving end, a reaction zone having an immobilized first binding partner, and a reagent releasing end having two releasable binding partners, at least one of which carries a label; (b) an absorbent pad; and (c) a separator positioned between the chromatographic element and the absorbent pad. Using an assay device of this third embodiment, the first complex is formed at the reaction zone between an analyte and a first binding partner bound to the reaction zone. The second reaction occurs at the reagent releasing end between the second and third binding partners once the aqueous solution has been added, to form a second complex bearing a label. The third reaction takes place in the reaction zone, when the [analyte:binding partner] first complex and the [second binding partner:third binding partner] second complex interact to form a third, labeled complex which can be detected. As in the embodiment described above, the second (embedded) binding partner is optionally a single antigen or a mixture of antigens, while the third (labeled) binding partner acting as the detector is optionally a generic reagent such as an anti-GST antibody.

The previous embodiments of the present invention address changes in the reagents used in the assay, and in the order in which the reactions take place. Yet another embodiment of the present invention involves the composition of the separator component of the assay device. Rather than using a barrier that must be manually removed during the assay, the separator can be composed of a material that will provide a "time-controlled" barrier, such as a semi-permeable membrane or a material that dissolves over time. When the device is in use as according to this embodiment of the present invention, by the time that the sample added to the sample receiving end has migrated laterally and covered the reaction zone, the separator will be dissolved or permeable, and the absorbent pad is readied for operation. An aqueous solution can then be added and the assay completed.

In yet other embodiments of the present invention, methods for detecting an analyte in a sample are provided, as are test kits employing the various embodiments of the assay device. Other permutations of the present invention are also possible, such as the simultaneous detection of multiple analytes using a single sample and a single device. Regardless of the embodiment employed, the assay device of the present invention does not need to include any additional filtration techniques using filters with special coatings, as employed in conventional lateral flow devices. The assay device is versatile and can be used to assess a variety of biological fluids or samples including, but not limited to saliva, serum, whole blood, urine, and solubilized fecal samples. This versatility is achieved by controlling the order in which the reactions occur, and by the additional "washing" of the reactants as provided by passage of the aqueous solution though the chromatographic element and into the absorbent pad.

An additional benefit of the present invention is that the simplicity of the design of the assay device provides a generic platform versatile enough to accommodate the needs and requirements for different product lines. An assay device specific for detection of a particular analyte can be easily adapted to detect a different analyte with minimal modification to the overall design, such as replacing the binding partner immobilized within the reaction zone, but still using a "generic" labeled binding partner for detection purposes. There is not any need for the development of additional specialized reaction reagents for the detection of each desired analyte. This not only reduces the time needed to design and produce new assay devices, but also significantly reduces the costs for product development. Furthermore, since the major components of the assay device are the same, manufacturing parameters can be maintained without major changes. Thus, a production facility for manufacture of a series of products based on the assay device of the present invention utilizes the same equipment and a minimal inventory of raw materials for the manufacture of all of the products, which in turn reduces the cost of operation significantly.

Additional objects, advantages and novel features of the invention will be set forth in part in the description which follows, and in part will become apparent to those skilled in the art upon examination of the following, or may be learned by practice of the invention.

BRIEF DESCRIPTION ON THE FIGURES

DETAILED DISCUSSION

Definitions

Figure 1A:
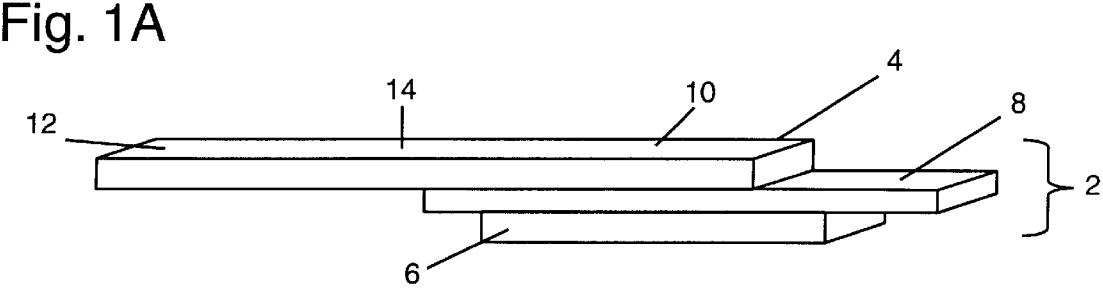
FIG. 1A depicts a schematic of a general view of an assay device of the present invention

Before describing the present invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a releasable binding partner" includes a combination of two or more such binding partners, reference to "an analyte" includes mixtures of analytes, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

The term "assay device" is used herein to describe a multi-component chromatographic apparatus used for the detection and/or measurement of one or more analytes of interest.

The term "chromatographic element" refers to a matrix (for example, a solid matrix or porous matrix) upon which the sample can be applied and allowed to migrate during the assay procedure.

The term "sample receiving end" refers to the portion of the chromatographic element at which the sample is administered or applied during the assay.

The term "reagent releasing end" refers to the portion of the chromatographic element distal to the sample receiving end, and at which one or more releasable assay reagents are incorporated.

The term "reaction zone" refers to the region of the chromatographic element between the sample receiving end and the reagent releasing end, within which one or more binding partners specific to the analyte (or to a complex containing the analyte) have been immobilized.

The term "absorbent pad" refers to an absorbent or bibulous material usually positioned at the base of the assay device.

The term "separator" refers to a barrier structure positioned between the chromatographic element and the absorbent pad.

The term "casing," "cassette," or "housing" as used herein refers to an optional component of the assay device, which surrounds at least a portion of the chromatographic element, absorbent pad and separator and provides some structural support.

The term "sample" refers to any desired material for sampling, usually of biological origin.

The term "analyte" refers to a compound or composition to be detected or measured in a sample.

The term "binding partner" is used herein to describe a member of a binding pair which interacts either chemically or physically to form a complex. An "immobilized" binding partner refers to a binding partner that is adsorbed, embedded or affixed, either permanently or semi-permanently, to a solid substrate or matrix (for example, the reaction zone of the chromatographic element.) A "releasable" binding partner refers to a molecule which is not permanently immobilized or affixed to a solid substrate or matrix, and is capable of migration or movement for example, by diffusion.

The term "GST" refers to one or more sequences derived from the enzyme glutathione S-transferase, an indicator molecule commonly incorporated into fusion proteins. Often this peptide sequence is positioned at the N-terminal region of a recombinant protein, where it can function as a leader sequence.

The term "label" as used herein refers to any substance that is capable of producing a detectable signal. Various labels suitable for use in the present invention include, but are not limited to, chromatogens, fluorescent or chemiluminescent compounds, catalysts, enzymes, enzymatic substrates, dyes, colloidal metallic and nonmetallic particles, and organic polymer latex particles. Particularly preferred for use in the present invention are the visually-detectable colored particles, such as colloidal metals and nonmetals, and dye particles.

The term "bibulous" refers to materials that are absorbent.

Methods and Systems

The present invention is directed toward assay devices for detection of one or more analytes in a sample. The assay devices are constructed in a manner to allow for the controlled release and interaction of the assay reagents. Further included in this invention are the methods for detecting the analyte, as well as test kits employing the assay device.

Analytes and Binding Partners

As will be understood by the ordinarily skilled artisan upon reading the specification, the analyte can be any specific substance or component that one is desirous of detecting and/or measuring in a chemical, physical, enzymatic, or optical analysis. Analytes of interest include, for example, antigens (such as antigens specific to bacterial, viral or protozoan organisms); antibodies, including those induced in response to an infection, allergic reaction, or vaccine; hormones, proteins and other physiological substances (for example, human chorionic gonadotropin, estrogens, progestins, testosterones, corticosteroids, human growth factors, hemoglobin, and cholesterol); nucleic acids; a variety of enzymes; therapeutic compounds and illicit drugs; contaminants and environmental pollutants; or any number of natural or synthetic substances.

As is appreciated by one skilled in the art, the number of natural and synthetic substances which can be detected by the assay devices and methods of the present invention is extensive, and include, but is not limited to, the following groups of compounds: ACE inhibitors; anti-inflammatory agents; anti-asthmatic agents; antidiabetic agents; anti-infectives (including but not limited to antibacterials, antibiotics, antifungals, antihelminthics, antimalarials and antiviral agents); analgesics and analgesic combinations; local and systemic anesthetics; various biocides (including, but not limited to, fungicides, insecticides, poisons, and toxins); cardiac and/or cardiovascular preparations (including angina and hypertension medications, anticoagulants, anti-arrhythmic agents, cardiotonics, cardiac depressants, calcium channel blockers and beta blockers, vasodilators, and vasoconstrictors); contraceptives, hormones steroids, growth factors, and the like; chemotherapies, including various antineoplastics; immunoreactive compounds, such as immunizing agents, immunomodulators, immunosuppressives; prescription and over-the-counter medications, including alcohol deterrents (for example, disulfiram), appetite suppressants, allergy medications, arthritis medications, diuretics and antidiarrheals, anti-emetics, antitussives, antipruritics, antipyretics, nausea medications, decongestants, antihistamines, muscle relaxants, antioxidants, herbal preparations and active component isolates, and vitamins; neurologically-active agents including Alzheimers and Parkinsons disease medications, migraine medications, adrenergic receptor agonists and antagonists, cholinergic receptor agonists and antagonists, anti-anxiety preparations, anxiolytics, anticonvulsants, antidepressants, anti-epileptics, antipsycotics, antispasmodics, psychostimulants, hypnotics, sedatives and tranquilizers; various combinations of these compounds, and the like.

The presence of antigens related to a variety of bacteria, viruses and/or parasites, or antibodies generated against one or more antigens, for example, during an immune response to one of these organisms, are detectable using the devices and methods of the present invention. Detectable prokaryotic systems include, but are not limited to, Aquifex, Archaeoglobus, Bacillus, Borrelia, Chlamydia, Escherichia, Helicobacter, Heliobacterium, Haemophillus, Methanobacterium, Methanococcus, Mycobacterium, Mycoplasma, Pyrococcus, Rickettsia, Synechocystis, and Trypanosoma (See, for example, the lists of microorganism genera provided by DSMZ-Deutsche Sammlung von Mikroorganismen und Zellkulturen GmbH, Braunschweig, Germany. Detectable viral systems include, but are not limited to, various strains of hepatitis; influenza (Orthomyxoviridae) and parainfluenza (Paramyxoviridae); adenoviruses; herpes viruses; variola, vaccinia and other pox viruses; polio and other picorna viruses (including enteroviruses and rhinoviruses); coronaviruses; rhabdoviruses (rabies); rubella and other togaviruses; papova viruses such as SV40, polyoma and papilloma viruses; various oncogenic viruses (Epstein-Barr virus, herpes simplex virus, cytomegalovirus); sarcoma viruses; and the like. For a general review, see Dulbecco and Ginsberg Virology (reprinted from Davis, Dulbecco, Eisen and Ginsberg's Microbiology, third edition (1980) Harper and Row, Philadelphia, Pa.).

In detecting bacteria, viruses and/or parasites of interest, any number of binding partners can be utilized in the assay devices of the present invention. For example, in the detection of host antibodies to *Mycobacterium tuberculosis,* antigenic peptide sequences such as CFP-10 (Dillon et al., (2000) J. Clin. Microbiology 38:3285–3290), Mtb81 (Henrickson et al., (2000) J. Clin. Microbiology 38:2354–2361), DPPD (Coler et al. (2000) J. Infectious Diseases 182:224–233), A60 (Cocito and Vanlinden (1986) Clin. Exp. Immunol. 66:262–272), LAM (Hunter et al. (1986) J. Biol. Chem. 261:12345–12351), ESTAT-6 (Andersen et al. (1995) J. Immunol. 154:3359–3372), 16-kDa HSP (Verbon et al. (1992) Clin. Exp. Immunol. 89:395–401), 24kDa antigen (Harboe et al. (1986) Infect. Immun. 52:293–302), 30-kDa antigen/85B (Salata et al. (1991) J. Lab. Clin. Med. 118:589–598) and 38kDa PhoS (Anderson and Hansen (1989) Infect. Immun. 57:2481–2488). Additional antigenic sequences which can be used as binding partners in the assay device include, but are not limited to, those described in PCT publications WO 00/55194 (Hendrickson et al.), WO 99/51748 (Skeiky et al.), WO 99/42118 (Reed et al.), WO 98/53076 (Alderson et al.), WO 98/53075 (Alderson et al.), WO 98/41533 (Jacobs et al.), WO98/32862 (Singh et al.), WO98/30699 (Guesdon and Chevrier), WO 98/36089 (Flohé), WO98/16646 (Reed, et al.), WO98/16645 (Reed, et al.), WO98/07847 (Magdelena et al.), WO97/44463 (Menozzi and Locht), WO97/09429 (Reed et al.), and WO97/09428 (Reed et al.). Alternatively, unique lipid structures or cell wall components can be employed, such as those described for *M. tuberculosis* in WO98/39025 by Verschoor et al. For the detection of antibodies to *H. pylori,* antigenic sequences such as those cited in WO98/49314 (Chow et al.), WO 99/48919 (Smith et al.), WO 98/56815 (Berglindh et al.), WO 98/32768 (Cripps et al.), WO 98/27432 (Quan et al.), WO 98/12562 (Chapman et al.), WO 97/28264 (Seo et al.), WO 97/21103 (Bernie et al.), and other like publications can be employed.

Additional such sequences (both nucleic acid sequences and/or peptide sequences) can be identified from a number of public and commercial databases, such as the GEN-BANK® and EST sequence databases (National Center for Biotechnology Information, the EMBL Nucleotide Sequence Database; Incyte's (Palo Alto, Calif.) LIFESEQ™ database, Celera's (Rockville, Md.) DISCOVERY SYSTEM™ database, and the like, by one of ordinary skill in the art.

Sample Sources

The device according to the present invention is particularly useful for detection of analytes in samples of biological origins. Such samples include, but are not limited to blood or serum; saliva, sputum, tears, sweat, or other secreted fluids; urine or fecal matter; as well as biologically derived fluids such as cerebrospinal fluid, interstitial fluid, cellular extracts and the like. A minimal volume of sample is used for the assay device of the present invention, particularly as compared to sample volumes used in a flow-through assay format. Desired sample volumes range from about 1 µL to about 500 µL, preferably from about 1 µL to about 100 µL, more preferably from about 5 µL to about 50 µL, most preferably between about 10 µL and about 30 µL.

The assay device of the present invention is based on binding assays such as, but not limited to, immunoassays. The binding partners involved in such binding assays include, but are not limited to, the following binding pairs: antibody and antigen or hapten; hormone and receptor; biotin and avidin; carbohydrate and lectin; effector and receptor molecules; enzymes and cofactors, substrates, or inhibitors; and complementary nucleotide sequences. Thus, the descriptions and examples included below are for demonstration purposes and should not be considered limiting to the particular applications addressed.

The devices of the invention are particularly well adapted to detecting antibody-antigen binding. Thousands of antibody-antigen binding partners are known and can be detected using the devices herein. A number of basic texts describe antibody-antigen interactions, antibody production processes, and other related matters, including, e.g., Borrebaeck (ed.) (1995) *Antibody Engineering, 2ⁿᵈ Edition* Freeman and Company, N.Y.; McCafferty et al. (1996) *Antibody Engineering, A Practical Approach* IRL at Oxford Press, Oxford, England; Paul (1995) *Antibody Engineering Protocols* Humana Press, Towata, N.J.; Paul (ed.) (1999) *Fundamental Immunology, Fourth Edition,* Lippincott-Raven, N.Y.; Coligan (1991) *Current Protocols in Immunology* Wiley/Greene, N.Y.; Harlow and Lane (1989) *Antibodies: A Laboratory Manual* Cold Spring Harbor Press, N.Y.; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256:495–497.

Assay Device Embodiments

FIG. 1A represents a simple illustrative embodiment of the assay device of the present invention. Assay device 2 is composed of chromatographic element 4, absorbent pad 6 and separator 8. Chromatographic element 4 includes three generally contiguous sections: sample receiving end 10, reagent releasing end 12, and reaction zone 14 positioned between sample receiving end 10 and reagent releasing end 12. The device is constructed such that separator 8 is positioned between chromatographic element 4 and absorbent pad 6, and can be removed to allow contact between sample receiving end 10 and absorbent pad 6 during operation of the device. Separator 8 can range in size from extending the entire length of chromatographic element 4, to covering only sample receiving end 10 of chromatographic element 4. In addition, a portion of separator 8 may extend beyond chromatographic element 4, at either sample receiving end 10 (as shown) or alternatively at reagent releasing end 12 of chromatographic element 4.

Chromatographic element 4 can be a nitrocellulose membrane, a porous matrix, a filter, or other like material. Assay reagents are incorporated into specific portions of chromatographic element 4. Sample receiving end 10 and/or reagent releasing end 12 of chromatographic element 4 can further comprise a layer of absorbent material, such as filter paper or a porous matrix, wherein additional assay reagents are incorporated. Absorbent pad 6 is prepared from any absorbent or bibulous materials (for example, filter paper) that will sufficiently draw and hold aqueous liquid when the assay device is in operation. In one embodiment, separator 8 is formed from an impermeable material, such as a thin piece of plastic, polyester, polycarbonate, or the like. In an alternative embodiment, separator 8 can be prepared from a material which will allow passage of an aqueous solution after a certain period of time, such as a semi-permeable membrane or a material which will dissolve upon exposure to liquid.

Figure 1B:
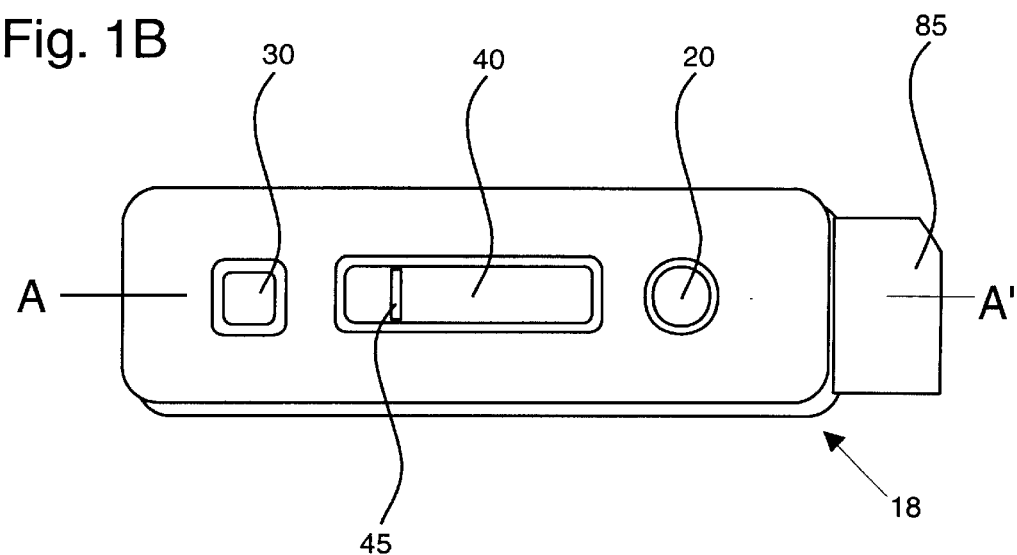
FIG. 1B depicts a schematic of an overhead view of a casing containing one embodiment of an assay device of the present invention.

FIG. 1B is a view of the upper face of one embodiment of the assay device according to the present invention. The assay device is enclosed in optional casing 18, formed from plastic, cardboard, treated paper, or other similar materials. Preferably, casing 18 has several windows, or openings, 20, 30 and 40, which are situated over the sample receiving end, the reagent releasing end, and the reaction zone of the chromatographic element, respectively. In FIG. 1B, visible indicator 45 (for example, a colored line) is marked on the reaction zone and can be seen through window 30. Alternatively, visible indicator 45 can be a marking on optional casing 18, at the side of window 40. In this embodiment of the device of the present invention, portion 85 of the separator protrudes from casing 18 to facilitate the removal of the separator during operation of the assay device. Alternatively, a different portion of separator 8 may protrude from the opposite end of casing 18, proximal to reagent releasing end 12, to permit partial removal of separator 8 from assay device 2, thus allowing absorbent pad 6 and sample receiving end 10 to come into contact.

Figure 2:
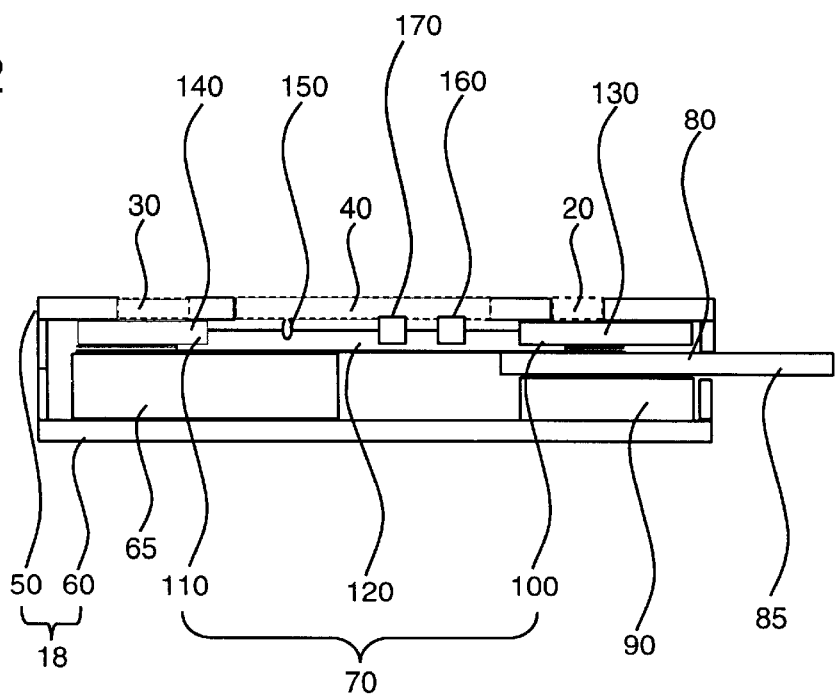
FIG. 2 depicts a cross-sectional view of a schematic of the casing and assay device of FIG. 1B, as viewed along line A–A'.

FIG. 2 illustrates a cross-sectional view of the assay device taken from FIG. 1B along line A–A'. Optional casing 18 consists of top portion 50 and bottom portion 60. Top portion 50 contains openings 20, 30 and 40 seen in FIG. 1B, whereas bottom portion 60 has support 65 which compensates for the difference in thickness between the two ends of the assembly. The design of casing generally ensures that various parts of the assay device are assembled firmly together within casing. Enclosed in casing 18 are three major components of the assay device: chromatographic element 70, which is positioned above separator 80, which in turn is positioned above absorbent pad 90. Chromatographic element 70 consists of sample receiving end 100, reagent releasing end 110, and reaction zone 120. Optionally, chromatographic element 70 can be attached to a backing layer. In this embodiment of the present invention, optional filter 130 is attached to and constitutes part of sample receiving end 100 of chromatographic element 70, while optional reagent-bearing pad 140 impregnated with releasable reagents is attached to and thus constitutes part of reagent releasing end 110. Reaction zone 120 contains colored indicator 150 as well as immobilized binding partner 160. Optionally, reaction zone 120 also contains known antibodies or known antigens (for example, Protein A) for use as control(s) 170.

A sample is applied to opening 20 that is positioned over sample receiving end 100 of chromatographic element 70. The sample is allowed to migrate laterally via capillary action towards reagent-receiving end 110 of chromatographic element 70. Separator 80 prevents the sample from flowing through chromatographic element 70 and into underlying absorbent pad 90. While the sample passes across reaction zone 120, the analyte (if present in the sample) will be able to bind to its specific binding partner 160 immobilized within reaction zone 120. Once the sample has covered reaction zone 120 (as indicated by the wetting front reaching colored indicator 150), an aqueous solution is added to opening 30 situated over reagent releasing end 110 of chromatographic element 70. Separator 80 is removed by pulling protruding end 85, allowing sample receiving end 100 of chromatographic element 70 and absorbent pad 90 to come into direct contact and reverse the direction of the liquid flow. The aqueous solution releases the assay reagents incorporated within reagent releasing end 110. The aqueous solution can be added prior to the removal of separator 80, concurrently with the removal, or immediately afterwards. A reagent such as a second specific binding partner labeled with a detectable label such as a naturally colored particle can then migrate into reaction zone 120 and react with the analyte-binding partner complex, enabling detection of the analyte. In addition, known antibodies or known antigens can be included in the chromatographic element as control(s) 170.

Figure 3A:
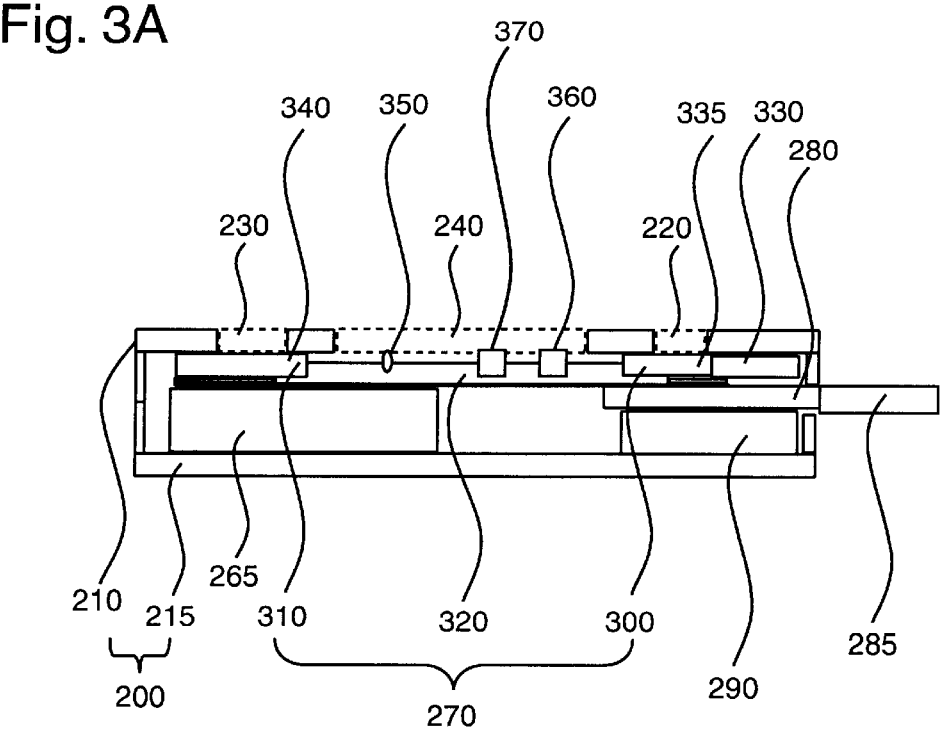
FIG. 3A depicts a cross-sectional view of a schematic of an alternative embodiment of the assay device of the present invention.
Figure 3B:
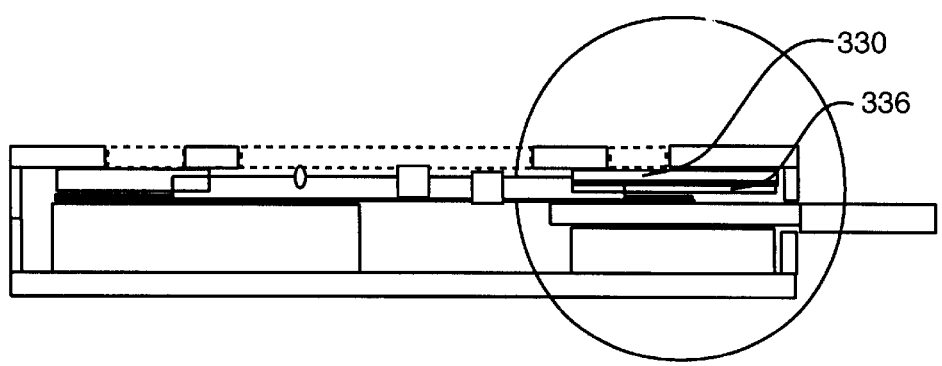
FIG. 3B depicts a cross-sectional view showing a schematic of an alternative arrangement of the sample receiving end of the assay device presented in FIG. 3A.

FIG. 3A depicts a cross-sectional view of another embodiment of the assay device of the present invention. This embodiment is preferred when a generic capture assay is desired. Similar to the embodiment in FIG. 2, optional casing 200 typically consists of top part 210 and bottom part 215. Top part 210 of casing 200 has openings 220, 230 and 240, whereas bottom part 215 has support 265 to compensate for the difference in thickness between the two ends of the assembly. Enclosed in casing 200 is chromatographic element 270, which is positioned above separator 280, which in turn is positioned above absorbent pad 290. Chromatographic element 270 consists of sample receiving end 300, reagent releasing end 310, and reaction zone 320. Optional filter 330 is attached to and constitutes part of sample receiving end 300 of chromatographic element 270, while optional reagent-bearing pad 340 impregnated with releasable reagents is attached to and constitutes part of reagent releasing end 310. Filter 330 can be subdivided into additional reagent bearing zone 335. Alternatively, as shown in FIG. 3B, additional filter 336 containing releasable reagents can be added for this purpose. Reaction zone 320 contains colored indicator 350 as well as immobilized binding partner 360, such as a capturing reagent specific for the target analyte.

In this embodiment of the present invention, a sample is applied to opening 220 that is located over sample receiving end 300 of chromatographic element 270. A first reaction takes place at sample receiving end 300 between the analyte (if present in the sample) and a first binding partner, released either directly from sample receiving end 300 or from reagent bearing zone 335 of optional filter 330. The analyte:first binding partner complex is allowed to migrate laterally by capillary action towards reagent-receiving end 310 of chromatographic element 270. Liquid impermeable separator 280 acts as a barrier preventing the sample from flowing through chromatographic element 270 and into underlying absorbent pad 290. When the sample passes across reaction zone 320, a second reaction occurs between the analyte:first binding partner complex and second binding partner 360 immobilized in reaction zone 320. Once the sample has covered reaction zone 320 (as indicated by the wetting front reaching colored indicator 350), separator 280 can be removed by pulling protruding end 285. Removal of separator 280 brings sample receiving end 300 of chromatographic element 270 and absorbent pad 290 into direct contact and reverses the direction of the liquid flow. An aqueous solution is added to opening 230 situated over reagent releasing end 310 of chromatographic element 270, thus releasing the assay reagents incorporated therein. The aqueous solution can be added prior to the removal of separator 280, concurrently with the removal, or immediately afterwards. A labeled reagent such as a third specific binding partner affixed with a detectable label such as a naturally colored particle, usually directed either toward the analyte or the analyte-containing complex, can then migrate into reaction zone 320 and react with the captured analyte-partner complex, thus enabling detection of the analyte. In addition, known antibodies or known antigens can be included in the chromatographic element as controls 370.

Figure 4A:
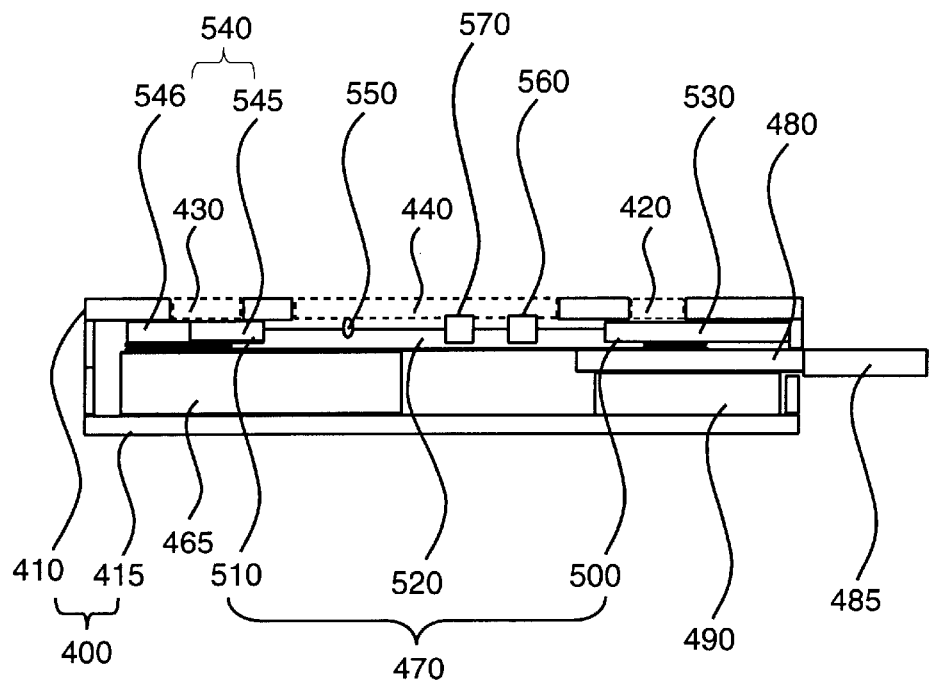
FIG. 4A depicts a cross-sectional view of a schematic of a third embodiment of the assay device of the present invention.
Figure 4B:
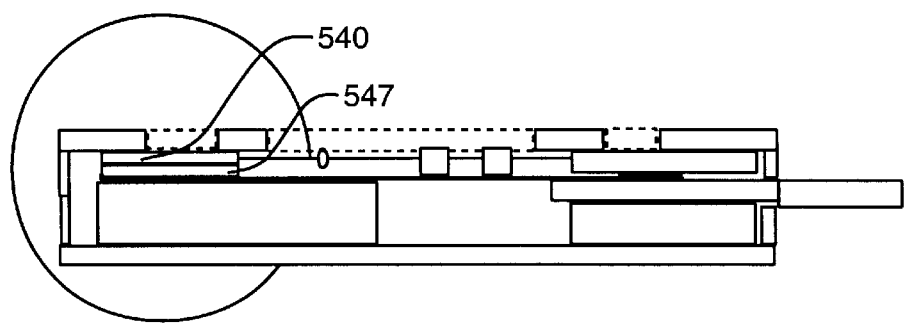
FIG. 4B depicts a cross-sectional view showing a schematic of an alternative arrangement of the reagent releasing end of the assay device presented in FIG. 4A.

Likewise, yet another embodiment of the assay device of the present invention can be constructed taking a similar approach, as depicted in FIG. 4A. Optional casing 400 typically consists of top part 410 and bottom part 415. Top part 410 of casing 400 has openings 420, 430 and 440, whereas bottom part 415 has support 465 to compensate for the difference in thickness between the two ends of the assembly. Enclosed in casing 400 is chromatographic element 470, which is positioned above separator 480, which in turn is positioned above absorbent pad 490. Chromatographic element 470 consists of sample receiving end 500, reagent releasing end 510, and reaction zone 520. Optional filter 530 is attached to and constitutes part of sample receiving end 500 of chromatographic element 470, while optional reagent-bearing pad 540 impregnated with releasable reagents is attached to and constitutes part of reagent releasing end 510. Reagent-bearing pad 540 can be subdivided into different zones 545, 546 to accommodate different releasable reagents or binding partners. Alternatively, as shown in FIG. 4B, one or more additional optional filters 547 impregnated with additional releasable reagents can be added to reagent releasing end 510 of chromatographic element 470. Reaction zone 520 contains colored indicator 550 as well as an immobilized binding partner 560, for example, a capturing reagent specific for the target analyte.

In this embodiment of the present invention, a sample is applied to opening 420 located over sample receiving end 500 of chromatographic element 470. The sample is allowed to migrate laterally by the capillary action towards reagent releasing end 510. The presence of separator 480 provides a liquid impermeable barrier, preventing the sample from flowing through chromatographic element 470 and into underlying absorbent pad 490. When the sample passes across reaction zone 520, a first reaction will take place between the analyte (if present in the sample) and first specific binding partner 560 immobilized in reaction zone 520. Once the sample covers reaction zone 520 (as indicated by the wetting front reaching colored indicator 550), separator 480 can be removed by pulling protruding end 485. Removal of separator 480 brings sample receiving end 500 of chromatographic element 470 and absorbent pad 490 into direct contact and reverses the direction of the liquid flow. An aqueous solution is added to opening 430 positioned over reagent releasing end 510. The aqueous solution can be added prior to the removal of separator 480, concurrently with the removal, or immediately afterwards. This addition of an aqueous solution allows not only release of the assay reactants immobilized within the reagent releasing end, but also enables a second reaction to occur between a second binding partner to the analyte and a third binding partner to the second binding reagent. The complex of second and third binding partners are driven from reagent releasing end 510 and across reaction zone 520, where a third reaction takes place between the two complexes. A label affixed to the third binding partner allows for detection of the complex and determination of the presence of the analyte. In addition, known antibodies or known antigens can be included in the chromatographic element as controls 570.

Figure 5A:
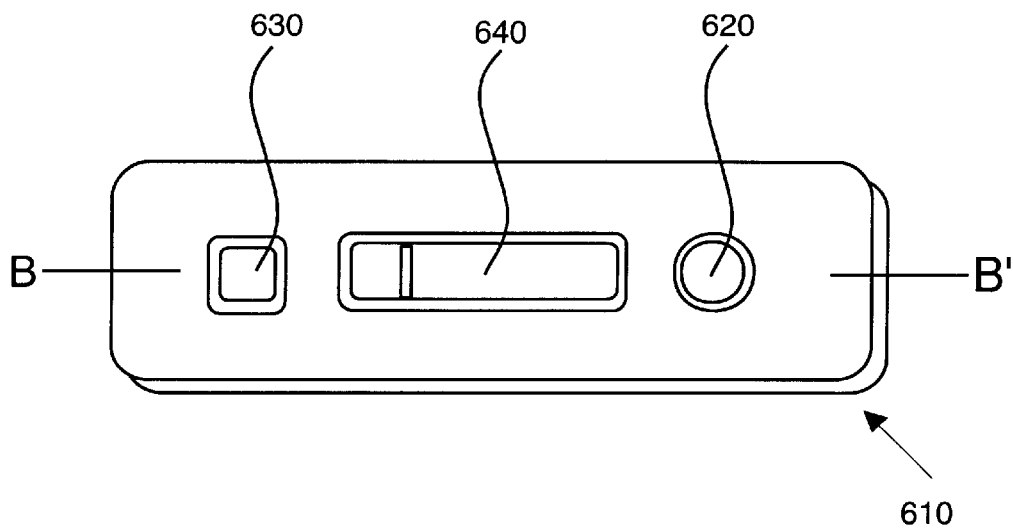
FIG. 5A depicts an overhead view of a schematic of a casing containing an assay device of the present invention showing an alternate arrangement of the separator.
Figure 5B:
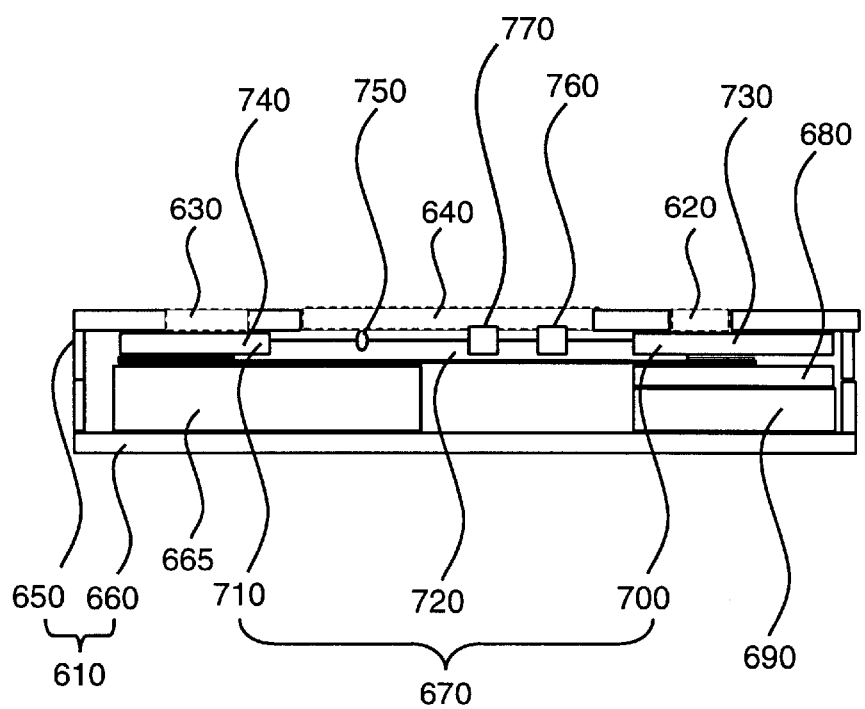
FIG. 5B depicts a schematic cross-sectional view of the casing and device of FIG. 5A, as viewed along line B–B'.

Referring to FIGS. 5A and 5B, a fourth embodiment of the present invention can be prepared using a construct similar to that of FIGS. 1B and 2A. In this embodiment, separator 680 is a time-controlled barrier such as a thin piece of semi-permeable material, or a material that will dissolve over time. Alternatively, several compositions which can be used as a dissolving-type separator include, but are not limited to, hydroxypropyl cellulose, polyethylene oxide, polyvinylpyrrolidone, poly(vinyl alcohol), poly(acrylic acid), polyacrylates such as Carbopol 934 (B. F. Goodrich), starch and starch derivatives, polysaccharides, sodium carboxymethyl cellulose, xanthan gum, karaya gum, and gelatin.

As in the previous embodiments, optional casing 610 consists of top part 650 and bottom part 660. Top part 650 of casing 610 has openings 620, 630 and 640, whereas bottom part has support 665 which compensates for the difference in thickness between the two ends of the assembly. The design of casing 610 ensures that various parts of the assay device are assembled firmly within casing 610. Enclosed in casing 610 is chromatographic element 670, which is positioned above separator 680, which in turn is positioned above absorbent pad 690. Chromatographic element 670 consists of sample receiving end 700, reagent releasing end 710 and reaction zone 720. In this embodiment, separator 680 is a time-controlled barrier such as a thin slide of semi-permeable or time-dissolving material. Separator 680 acts as a barrier to the flow of liquid into underlying absorbent pad 690 for a limited period of time (between 10 seconds and 10 minutes, more preferably between 30 seconds and 5 minutes, most preferably for approximately 1 minute). Optional filter 730 is attached to and constitutes part of sample receiving end 700 of chromatographic element 670, while optional reagent-bearing pad 740 containing one or more releasable reagents is attached to and constitutes a part of reagent releasing end 710. Reaction zone 720 contains colored indicator 750 as well as immobilized binding partner 760.

When this particular embodiment of the assay device is used, the sample is applied to opening 620 situated over sample receiving end 700 of chromatographic element 670. The sample is allowed to migrate laterally via capillary action towards reagent-receiving end 710. Separator 680 prevents the sample from flowing towards underneath absorbent pad 690 for a predetermined length of time (as determined by the composition and thickness of the separator). A reaction between an analyte (if present in the sample) and its specific binding partner 760 immobilized in reaction zone 720 will take place while the sample passes across this region. By the time that the sample has covered reaction zone 720 (as indicated by the wetting front reaching colored indicator 750), separator 680 will have either become permeable or dissolved completely. In either case, the absence of separator 680 allows sample receiving end 700 of chromatographic element 670 to come into fluid communication with absorbent pad 690, reversing the direction of the liquid flow. An aqueous solution can be added to window 630 positioned over reagent releasing end 710, thus releasing the assay reagents incorporated therein. A reagent such as a second specific binding partner labeled with a detectable label such as a naturally colored particle can then migrate into reaction zone 720 and react with the analyte-binding partner complex, enabling detection of the analyte. In addition, known antibodies or know antigens can be included in the chromatographic element as controls 770.

Figure 6:
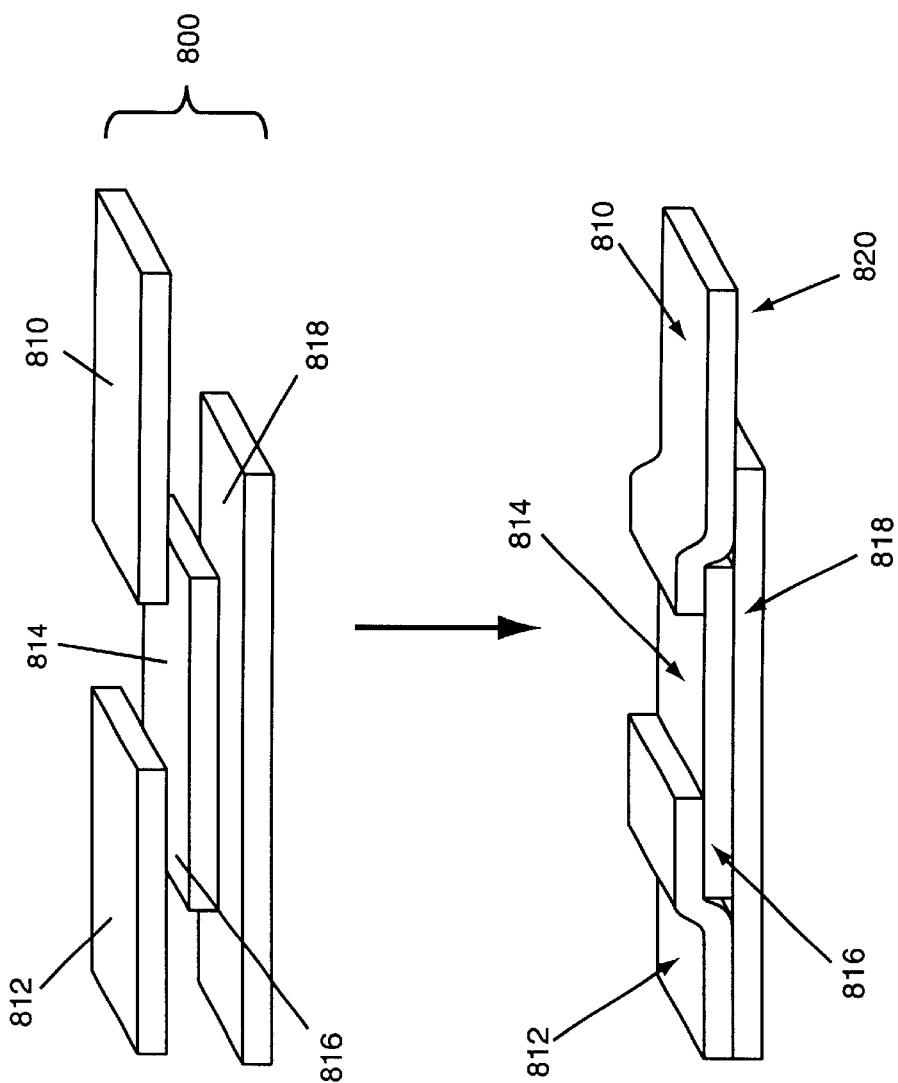
FIG. 6 is a schematic showing details of assembly of an example chromatographic element.

FIG. 6 shows details of assembly of example chromatographic element 800. As shown, sample end 810, reagent end 812 and membrane 816 comprising reaction zone 814 are mounted on adhesive backing 818, such that sample end 810 comprises area without backing 820 for subsequent contact with an absorber pad.

Additional Features

The present invention also addresses assay devices for the detection of multiple disease markers, such antigens to HIV and HTLV, such that the simultaneous detection of different diseases can be performed using a single sample of biological fluid and a single assay device. Multiple disease markers, for example, antigens to different pathogens, can be immobilized within the reaction zone of the chromatographic element. This embodiment of the present invention would enable a single device to be used for detection of multiple analytes from a given sample. Similarly, antibodies such as anti-human IgG or IgM can be immobilized on the reaction zone of the chromatographic element, as shown in FIGS. 3 and 4. Such a construct allows a single device using a generic detector such as a labeled specific binding partner for detection of different types of antibodies to the same pathogen.

The assay devices of the present invention are able to provide improved sensitivity for analyte detection over current available rapid chromatographic assays without compromising in the specificity. This advancement is demonstrated in the example section of the present invention. However, the advantages of the present invention are not limited to the functional aspects of the assay device, but address the practical aspects as well. Regardless of the particular embodiment employed, an assay device based on the present invention does not need to include additional filtration devices, such as filters with special coatings, to handle a wide variety of biological fluids. This versatility is achieved by the design of the assay device, which allows staged reactions and sufficient washing without involving additional steps.

An additional advantage of the assay devices of the present invention is in the ease of manufacture of the assay device. The devices of the present invention employ a generic construct, which can be modified with minimal alteration from one application to another. This generic platform is versatile enough to accommodate the needs and requirements for multiple product lines. A product specific for detection of a particular analyte can be easily adapted to another product for a different analyte with minimal modification of the overall design of the assay device, such as replacement of the binding partner to one particular analyte. Accordingly, it is not necessary to develop additional specific detecting reagents for each specific product. Rather, the specificity of the reaction is determined by the first binding partner while the labeled binding partner can be a multipurpose generic construct (for example, anti-human antibodies or anti-GST antibodies labeled with a detectable label such as a naturally colored particle). This is a huge advantage as compared to the development of traditional rapid assays, in which a specific detector for a specific product must be developed for each assay, in order to maintain an acceptable sensitivity. The present invention therefore reduces both the time and the cost used for product development. Furthermore, since the major components of the assay device can be used across a variety of assays, production parameters can be maintained without changes. A production facility manufacturing a series of products based on the present invention would use a single set of manufacturing equipment and a minimal array of inventories of raw materials, which in turn significantly reduces the costs of operation.

EXAMPLES

The following examples are offered for illustration. One of skill in the art will recognize a variety of noncritical parameters that can be changed.

Example 1

Assay devices for the detection of human antibodies to HIV types 1 and 2 were prepared as follows. Recombinant HIV 1 antigens p24 and gp41, and recombinant HIV 2 antigen gp36, were immobilized, or "slotted", at a concentration range of about 0.08 to about 0.3 mg/ml onto a nitrocellulose membrane of 8 $\mu$m average pore size (Whatman, Ann Arbor, Mich.) using an IVEK (IVEK Corporation, N. Springfield, Vt.) Multispense 2000 striping machine. Protein A was immobilized in the same manner for use as an assay control line. The membrane was dried for approximately 10 minutes before addition of a blocking buffer (Milli-Q purified water with 0.3% casein and 0.25% sucrose). The membrane was exposed to the blocking buffer for approximately 1 minute, after which the membrane was dried at 37° C. for another 15 minutes. The membrane was finally affixed to a membrane backing (Adhesives Research Inc., Glen Rock, Pa.).

A reagent-bearing pad was prepared using a porous matrix (Hollingsworth & Vose, Inc., East Walpole, Mass.). The pad was sprayed with goat anti-human IgG antibodies (Zymed Laboratories Inc., South San Francisco, Calif.) that were labeled with colloidal gold particles of approximately 40 nm, and dried at 37° C. for 30 minutes. A chromatographic element was prepared by affixing an untreated porous matrix to one end of the nitrocellulose strip and the reagent-bearing pad to the other end of the nitrocellulose strip. The assembly was then cut into strips of about 4 mm by about 56 mm in size to form a chromatographic element having the untreated porous matrix at the sample receiving end, the reagent-bearing pad attached at the reagent releasing end, and the antigens immobilized in the reaction zone region. An assay device was assembled by placing an absorbent pad in the bottom half of a casing, then laying a separator above the absorbent pad, such that one edge of the separator extended from the casing. The chromatographic element was situated on top of the separator (such that the sample receiving end was positioned above the separator) and the top half of the casing was attached.

A serum sample (approximately 15 µl) was added to the sample receiving end of the chromatographic element via a first opening, or window, on the casing. The sample was allowed to migrate laterally and cover the reaction zone region of the membrane, as determined by viewing the progression of the wetting front through an opening in the casing directly above the reaction zone. Any human antibodies to the three HIV antigens present in the sample were bound to these antigens as the sample fluid crossed the region at which the antigens are bound to the nitrocellulose membrane (the reaction zone). When the sample reached the indicator in the reaction zone after approximately 1 minute, three drops (approximately 120 µL) of aqueous solution (reagent releasing buffer, comprised of 0.01M phosphate buffered saline pH 7.4 plus 0.4% SDS) were added to a second opening on the casing located above the reagent releasing end of the chromatographic element. Addition of the aqueous solution solubilized the releasable binding partner (in this example, the colloidal gold-labeled goat anti-human IgG antibodies). Immediately after addition of the aqueous solution, the separator was removed from the assay device by pulling on the protruding end, thus allowing the chromatographic element and the absorbent pad to come into contact. The labeled goat anti-human IgG antibodies were then allowed to migrate across the reaction zone of the chromatographic element and bind to any human IgG antibodies immobilized in this region. The results were readable in approximately 5 minutes through the opening in the casing. Typically, a negative result is indicated by the appearance of a single control line in the reaction region. Bands representing either one or both of the disease markers will also appear if the analyte(s), in this case anti-HIV antibodies, are present.

To demonstrate the sensitivity of this assay, a titration-end point activity test was performed. Samples positive for HIV 1 (SBA033) or HIV 2 (SBB043) were serially diluted to generate a series of sample concentrations. These diluted samples were tested in parallel with both the device described in Example 1 and two commercially-available test kits (Instant-check "flow-through" device, Genelabs Diagnostics, Singapore; HIV 1/2 Stat-Pak "lateral flow" device, Chembio Diagnostics Systems Inc., New York, USA). As a negative control, two HIV-negative samples (NAA196 and NAA 237) were employed. The intensity of the resulting band or bands were scored visually, and recorded as 3+ or 2+ if the intensity was greater than that of the control band, and 1+, ± and ±− if the intensity was less than that of the control band.

The results of this experiment, as tabulated in Table 1, clearly demonstrate the improved sensitivity of the present invention as compared to commercially available test kits employing conventional lateral flow or flow-through technologies.

TABLE 1

A comparison of titration-end point activity of samples positive for HIV with three assay embodiments

| Serum Sample | Dilution | Example 1 Device | Lateral flow | Flow through |
|---|---|---|---|---|
| SBA033 | no dilution | 3+ | 2+ | 3+ |
| | 1:16 | nd | +/− | nd |
| | 1:32 | 3+ | − | 3+ |
| | 1:64 | 2+ | − | 2+ |
| | 1:128 | 2+ | − | 2+ |
| | 1:256 | 2+ | − | 2+ |
| | 1:512 | 2+ | − | 1+ |
| | 1:1024 | 1+ | − | +/− |
| SBB043 | no dilution | 2+ | 2+ | 3+ |
| | 1:16 | nd | 1+ | nd |
| | 1:32 | 1+ | +/− | 1+ |
| | 1:64 | 1+ | − | 1+ |
| | 1:128 | +/−− | − | 1+ |
| | 1:256 | +/−− | − | +/− |
| | 1:512 | +/−− | − | +/−− |
| | 1:1024 | − | − | − |
| NAA196 | no dilution | − | − | − |
| NAA237 | no dilution | − | − | − |

Example 2

Assay devices for the detection of human antibodies to *Helicobacter pylori* were prepared in a manner similar to that described in Example 1. Briefly, a nitrocellulose membrane of 8 µm average pore size was slotted with one or more native or recombinant antigens of *H. pylori* at a concentration of approximately 0.6 mg/ml using the IVEK striping machine. Exemplary recombinant antigens include, but are not limited to, the *H. pylori* antigens described in WO98/49314. The membrane was dried for 10 minutes before blocking with a blocking buffer (Milli-Q purified water with 0.3% casein and 0.25% sucrose) for 1 minute. The blocked membrane was then dried at 37° C. for another 15 minutes before being affixed to a membrane backing. A reagent-bearing pad was prepared using a porous matrix and sprayed with goat anti-human IgG antibodies that were labeled with colloidal gold particles of approximately 40 nm. The reagent-bearing pad was also dried at 37° C. for 30 minutes prior to use. The chromatographic element was prepared by affixing a porous matrix to the sample receiving end of the membrane-backed nitrocellulose strip and the reagent-bearing pad to the reagent releasing end of the strip, such that the immobilized *H. pylori* antigen was situated in the reaction zone between the two ends. The assembly was then cut into a strip approximately 4 mm by 56 mm in size. An assay device was assembled by placing an absorbent pad in the bottom half of a casing, followed by a separator, and lastly the chromatographic element before closing the top half of the casing.

Approximately 30 µl of serum sample was added to the sample receiving end of the chromatographic element via a first window on the casing. The sample was allowed to migrate laterally and cover part of the nitrocellulose membrane. When the sample reached the indicator in the reaction zone (after approximately 1 minute), three drops (approximately 120 µL) of reagent releasing buffer (of 0.01 M phosphate buffered saline pH 7.4 plus 0.4% SDS) were added to a second window on the casing, releasing the colloidal gold labeled goat anti-human IgG antibodies (the releasable binding partner) incorporated therein. The separator was then removed by pulling the end protruding from the device casing, to allow the chromatographic element and the absorbent pad to come into contact. The labeled goat anti-human IgG antibodies were then allowed to migrate across the reaction zone of the chromatographic element and bind to any human IgG antibodies immobilized in this region. The results generated by the assay device can be read in approximately 5 minutes through the third window that is directly situated on the reaction zone. Typically, a negative result will be indicated by the appearance of a control line only in the window. Another band representing the [*H. pylori* antigen:human antibody: labeled goat anti-human IgG] complex will also appear if the analyte, in this case the anti-*H. pylori* antibody, is present in the sample.

In a titration-end point activity test, a sample from an individual infected with *H. pylori* (sample W003) was serially diluted, and the diluted samples were tested with both the device of the present invention and a device constructed according to conventional lateral flow assay design. As a negative control, a sample negative for *H. pylori* (sample H5) was employed, The results of the experiment are presented in Table 2. The data clearly demonstrate the improved sensitivity of the assay device of the present invention as compared to a device of the conventional lateral flow design.

TABLE 2

A comparison of titration-end point activity of a sample positive for *H. pylori* with two devices

| Sample | Dilution | Lateral Flow Device | Device based on present invention |
|---|---|---|---|
| W003 | no dilution | +/− | 2+ |
|  | 1:2 | +/− | 2+ |
|  | 1:4 | +/−− | 1+ |
|  | 1:8 | − | +/− |
|  | 1:16 | − | +/− |
|  | 1:32 | − | +/− |
| H5 | no dilution | − | − |

In another comparison study, a panel of samples either positive or negative for *H. pylori* was assayed using both devices of the present invention and a commercially available Western Blot assay (Helico Blot 2.1, Genelabs Diagnostics, Singapore). The negative samples were from healthy donor, whereas the positive samples were from patients infected with *H. pylori* as confirmed by at least two of the following methods: histology, culture, and rapid urease test. The results of the assays are presented in Table 3. Devices of the present invention were shown to provide a slight improvement of detection specificity without compromising the sensitivity of the assay.

TABLE 3

A comparison study between Western Blot and devices of present invention

| Sample Tested | Western Blot Reactivity | Assay Device Reactivity |
|---|---|---|
| Positive Samples | 28/30 (93%) | 28/30 (93%) |
| Negative Samples | 3/25 (12%) | 2/25 (8%) |

Example 3

An experiment was also performed with the *H. pylori* assay device as prepared in Example 2 using saliva samples instead of serum samples. Saliva samples from a healthy individual and an *H. pylori* infected individual, as confirmed by a Western blot test, were collected and diluted 1:5 in phosphate buffer saline (0.01M, pH 7.4). The samples were centrifuged for 5 minutes at 12,000 rpm and then stored in a freezer at −20° C. before use. Approximately 30 µl of each sample was applied to separate assay devices and tested according to the assay procedure described in Example 2. As a negative control, an assay using only phosphate buffer saline (0.01 M, pH7.4) was included in the experiment. The saliva sample from the infected individual produced a defined control band as well as an infection-indicating band with intensity in the range of 1+ to 2+. Neither the saliva sample from the healthy individual nor the PBS experiment control gave rise to an infection-indicating band. The saliva sample at the same 1:5 dilution was not detected by a conventional lateral flow format using the same reagents. The results of this experiment, therefore, demonstrated not only the improved sensitivity of the device of the present invention, but also that the device can be used for detection of anti *H. pylori* antibodies in saliva without the need for any structural modification to the device.

Example 4

In another experiment performed with the assay device as prepared in Example 2, whole blood samples were used in place of serum samples. Whole blood samples were collected from healthy individuals and an *H. pylori* infected individual, as confirmed by a Western blot test. Approximately 50 µl of each of the samples were applied to separate assay devices and tested as according to the assay procedure described in Example 2. The whole blood sample from the infected individual produced a defined control band as well as an infection-indicating band having an intensity of 3+. In contrast, the whole blood samples obtained from healthy individuals (n=13) produced only the control band and not the infection-indicating band. For comparison, the whole blood samples were also tested using a conventional lateral flow assay prepared using the same reagents. In the conventional lateral flow assay, higher backgrounds were produced, rendering interpretation of the assay results difficult. This comparison demonstrated that the assay device of the present invention can be used for detection of anti *H. pylori* antibodies in whole blood samples without the need of a structural modification to the device. In addition the results showed that the assay device based on the present invention was not affected by the high background problems that arose in the conventional lateral flow format.

Example 5

Alternative embodiments of the assay devices for detection of *H. pylori* were prepared as follows. Two purified *H.*

*pylori* recombinant proteins, such as those disclosed in PCT publication WO98/49314, were prepared in dilution buffer (0.15M NaCl, 0.04M $Na_2HPO_4$, 6mM $NaH_2PO_4$, 60 mM sucrose and 7.6 mM $NaN_3$ in Milli-Q water) and loaded, or "striped," onto 8 µm pore size nitrocellulose membranes using a BIODOT® (Irvine, Calif.) XYZ3000 spraying machine. One antigen is used as a "current infection marker" (i.e. an antigen that decreases after eradication of the disease), while a second antigen provides an indication that the patient has been exposed to the disease (i.e., the antigen does not disappear with recovery from the disease state). In addition to these antigens, an assay control line was also striped onto the membrane using a 0.02 mg/ml solution of protein A.

The striped membranes were dried at 37° C. for 30 minutes before being immersed for 1 minute in a blocking buffer consisting of 0.125% casein, 0.125% polyvinyl pyrollidone (PVP), 0.05% Triton, and 1:75 parts of STABIL-COAT™ (SurModics Inc., U.S.A.) in Milli-Q H20. The membranes were subsequently dried at 37° C. for 1 hour.

The reagent-bearing pad was prepared using a porous matrix from Hollingsworth & Vose, Inc. (East Walpole, Mass.). The porous matrix was sprayed with goat anti-human IgG antibodies that were labeled with colloidal gold particles of 30–40 nm. The reagent-bearing pad was then dried at 37° C. for 2 hours prior to incorporation into the device. The chromatographic elements were constructed, and the assay devices were assembled as described in the previous examples. The regions of the chromatographic element containing the protein A control and the antigens are positioned such that they are proximal to a window region in the device housing.

For this experiment, several different sera collections were employed to test the devices. The United Kingdom (UK) sera were provided by Dr. Rathbone at Medical Device Agency, Leicester, UK.; the USA panel A sera were provided by Dr. Hartley Cohen at University of Southern California, San Diego, USA; the USA panel B sera were provided by Dr. Roost from Veterinary Hospital at Burlingame, Calif., USA; the Italian panel of sera was provided by Dr. Gasbarrini from University Catholica, Rome, Italy; and the Hong Kong panel was provided by Dr. Joseph Sung from Prince of Wales Hospital, Hong Kong. All sera were characterized using the standard *H. pylori* tests of culture, histology, urea breath test, and/or rapid urease test. A positive *H. pylori* serum is defined as having a positive result in any two of these four "gold standard" tests.

To perform the assay, 25 µl of serum was added to the sample receiving end of the assay device, and the serum front was allowed to migrate past the indicator line on the top of the device. Two drops of chase buffer (about 30 µl per drop of a solution containing 0.3M NaCl, 0.04M $NaH_2PO_4$ and 0.15% SDS in Milli-Q water) was then dispensed into the reagent receiving end of the assay device, and allowed to soak into the reagent bearing pad. The separator was pulled from the device, allowing the chromatographic element and the absorbent pad to come into contact. The chase buffer, which now also contains the reconstituted gold conjugate previously deposited onto the reagent bearing pad, and the serum were then allowed to migrate across the reaction zone in a reverse direction. The assay result was typically obtained within 15 minutes by examining the assay device for the presence or absence of the antigen bands and the protein A control band.

The assay devices of the present invention (GLD ASSURE™ *H. pylori* test kit) were compared to two competitor rapid test kits, SURESTEP™ (Applied Biotech Inc., San Diego, USA) and PYLORISET®Screen II (Orion Diagnostica, Espoo, Finland). A comparison of the sensitivities and specificities of the assay devices are shown in Table 4 below.

TABLE 4

A comparison of sensitivities and specificities for three devices for the detection of antibodies to *H. pylori*

| Sera sample | ASSURE ™ device | SURESTEP ™ device | PYLORISET ® Screen II |
|---|---|---|---|
| UK panel | | | |
| Sensitivity (%) | 93 | 93 | 96 |
| Specificity (%) | 93 | 93 | 37 |
| USA (Cohen) | | | |
| Sensitivity (%) | 97 | 93 | 100 |
| Specificity (%) | 96 | 100 | 56 |
| USA (Roost) | | | |
| Sensitivity (%) | 100 | n.d. | 96 |
| Specificity (%) | 100 | n.d. | 71 |
| Italian | | | |
| Sensitivity (%) | 94 | 83 | 98 |
| Specificity (%) | 88 | 84 | 56 |
| Hong Kong | | | |
| Sensitivity (%) | 94 | n.d.[a] | n.d.[a] |
| Specificity (%) | 90 | n.d.[a] | n.d.[a] | n.d. = not determined
[a] = unable to run tests due to shortage of sera samples

As shown in Table 4, the sensitivities and specificities of the ASSURE™ device were greater than 90% in all of the samples tested, except for the specificity in the Italian sample. In contrast, the other two devices had a lower sensitivity (83%) or specificity (37%). This finding is consistent with those previously reported. The sensitivities of some rapid tests can be as low as 82% and specificities as low as 63% (Leung, supra). In addition, it was noted that the assay devices employed in this experiment were more robust than the commercially available kits. The assay devices of the present invention provided test results in which the intensity of the bands remained the same beyond the 15 minute time point for measurement, whereas the intensity of the bands continued to increase with the other two kits tested, leading to false positives. Thus, the assay device of the present invention also provides a permanent record of the test result.

Example 6

The assay devices as described in Example 5 were also examined for their utility in monitoring treatment for *H. pylori*, as compared to the SURESTEP™ and Pyloriset®Screen II kits. By providing both an antigen that indicates exposure to *H. pylori*, as well as a second antigen that indicates the status of the infection, the assay kits of the present invention provide a novel device for monitoring progress, decrease, and/or eradication of *H. pylori* infections.

In one example, patient E5 was tested positive by histology and rapid urease test before treatment with antibiotics. At the 6 month time point, the patient was tested by urea breath test (UBT) and was confirmed negative. This represents a case of successful treatment therapy. Sera was collected from this patient before treatment, as well as at 1, 3, and 6 months after treatment and subsequently tested with the rapid test kits. The results (as showed in Table 5) were recorded as intensities of the test bands: 1+=weak intensity, 2+=medium intensity, 0=no intensity (i.e., non-reactive). The results showed that the ASSURE™ assay device indicated eradication of the disease at an earlier timepoint than the other devices examined.

TABLE 5

Comparison of H. pylori assay results for three devices during successful antibiotic treatment

| time point | ASSURE ™ device | SURESTEP ™ device | PYLORISET ® Screen II |
|---|---|---|---|
| E5-0 months | 1+ | 1+ | 1+ |
| E5-1 month | 1+ | 1+ | 1+ |
| E5-3 months | 0 | 1+ | 1+ |
| E5-6 months | 0 | 1+ | 1+ |

In a second example, patient E16 was also tested positive by histology and rapid urease test before treatment with antibiotics. At 6 months, the patient was tested by urea breath test and was confirmed positive. This represents a case of failed treatment therapy. Sera was collected from the patient before treatment, as well as at 1, 3, and 6 months after treatment and subsequently tested with the test kits. In this case, concordance results were obtained between the two rapid tests as well as with the urea breath test (Table 6).

TABLE 6

Comparison of H. pylori assay results for two devices during unsuccessful antibiotic treatment

| time point | ASSURE ™ device | PYLORISET ® Screen II |
|---|---|---|
| E16-0 months | 2+ | 2+ |
| E16-1 month | 2+ | 2+ |
| E16-3 months | 2+ | 2+ |
| E16-6 months | 2+ | 2+ |

Example 7

Assay devices for the detection of human antibodies to *Mycobacterium tuberculosis* (ASSURE™ TB Rapid Test) were prepared in a manner similar to that described in Example 1. A nitrocellulose membrane of 8 μm average pore size was sprayed with a proprietary tetra-fusion recombinant protein which contains four *M. tuberculosis* antigens (such as those described in WO99/51748), at a concentration of approximately 0.41 mg/ml using a BioDot spraying machine. The nitrocellulose membrane was dried for 10 minutes before immersing the membrane for 1 minute in a blocking buffer (Milli-Q purified water containing 6.7% of STABILCOAT® (SurModics, Inc. U.S.A.), 0.05% Triton, and 0.5% casein). The blocked membrane was then dried in 37° C. for 60 minutes before being affixed to a membrane backing.

The reagent-bearing pad was prepared using a porous matrix from Hollingsworth & Vose, Inc. (East Walpole, Mass.). The porous matrix was sprayed with goat anti-human IgG antibodies that are labeled with colloidal gold particles of 30–40 nm. The reagent-bearing pad was then dried at 37° C. for 2 hours prior to incorporation into the device. The chromatographic element was prepared by affixing an untreated porous matrix to one region of the blocked nitrocellulose/backing laminate, and the reagent-bearing pad to another region. This assembly was then cut into a strip approximately 4×56 mm² in size, having the untreated porous matrix at the sample receiving end, the reagent-bearing pad attached at the reagent releasing end, and the antigens immobilized in the reaction zone region of the strip. The assay device was assembled by placing an absorbent pad in the bottom half of a cassette, then laying a separator above the absorbent pad, such that one edge of the separator extended from the cassette. The chromatographic element was situated on top of the separator (such that the sample receiving end was positioned above the separator) and the top half of the cassette was attached.

Example 8

The assay devices of Example 5 were used to test patient serum samples obtained from World Health Organization (WHO) Specimen Bank. A total of 198 patient samples were collected from symptomatic individuals with or without tuberculosis, 108 sample from TB-positive patients and 90 samples from TB-negative patients. The TB status was determined by a positive result in one or more tests, including AFB (acid-fast bacilli) microscopy, sample culture, and chest X-ray. The TB positive group included 67 specimens from patients with co-existing TB/HIV infections and 41 specimens from patients with only TB. Similarly, the non-TB group included 41 specimens from HIV infected patients, and 55 specimens from non-HIV infected patients. An additional 59 serum specimens derived from normal healthy donors were purchased from BioClinical Partner Inc. (Franklin, Mass.) and included in the study.

The assays using the described patient samples were performed as follows. A serum sample approximately 25 μl in volume was added to the specimen window (sample receiving end) of the assay device. The sample was allowed to migrate laterally and cover part of the chromatographic element. When the sample reached an indicator in the viewing window (after approximately 30 seconds), three drops of reagent-releasing cum washing buffer (Milli-Q purified water with 50 mM $NaH_2PO_4$, 300 mM NaCl, and 0.1% SDS, pH8.0) were added to the buffer window (reagent releasing end), resulting in the release of the colloidal gold labeled goat anti-human IgG antibodies from the reagent pad. The separator was then removed from the assay device by pulling upon the protruding end, to allow the chromatographic element and the absorbent pad to come into contact. (In an alternative embodiment, the separator is not completely removed from the device, but rather it is shifted such that the chromatographic element and the absorbent pad are able to come into contact with one another.) The colloidal gold labeled goat anti-human antibodies were then allowed to migrate across the reaction zone, where they interacted with any human antibodies bound to the TB antigen.

The result generated by the assay device can typically be read in approximately 10 minutes, by monitoring the chromatographic element through the viewing window. Optionally, a negative result will be indicated by the appearance of a control line only, whereas a positive result will have both the test line and the control line appeared in the viewing window.

The assay devices of the present invention detected 79% (19/24) of the smear positive patients without HIV co-infection (Table 7). In addition, the assay devices detected an additional 10 cases of proven TB from smear test negative patients without HIV co-infection (n=17), giving a detection percentage of 59%. With the proven TB patients having HIV co-infection, the detection rates of the assay devices were 42% for both smear test positive (10/24) and smear test negative (18/43) groups (Table 7). Furthermore,

TABLE 7

Performance of Assure ™ TB Rapid Test in AFB tested positive or negative tuberculosis patients with or without HIV co-infection

| Status | | No. of samples | Rapid Test Positive | Percentage of detection by Rapid Test | Specificity by Rapid Test |
|---|---|---|---|---|---|
| HIV negative | AFB positive | 24 | 19 | 79% | — |
| HIV negative | AFB negative | 17 | 10 | 59% | — |
| Total | — | 41 | 29 | 71% | — |
| HIV positive | AFB positive | 24 | 10 | 42% | — |
| HIV positive | AFB negative | 43 | 18 | 42% | — |
| Total | — | 67 | 28 | 42% | — |
| Donor | — | 59 | 3 | — | 95% |

The assay device of the present invention was also compared with smear test and culture, individually or combined, in detecting proven TB. As shown in Table 8, the smear test detected 59% (24/41) of the TB only group, and 36% (24/67) of the TB/HIV co-infected group, yielding a total sensitivity of 44% (48/108). Culture alone, on the other hand, detected 56% (23/41) and 55% (34/67) of the same respective groups, providing an improved total sensitivity of 53% (57/108). The assay devices of the present invention, however, provided an even higher sensitivity in the TB group without HIV co-infection, detecting 71% (29/41) of such proven cases of TB. The detection rate was 42% (28/67) in the TB/HIV co-infected group. Thus, the assay devices produced an overall sensitivity of 53% (57/108), comparable to that of the culture method (Table 8). When combined, smear and culture tests yield a sensitivity of 63% (26/41), 55% (37/67) and 57% (62/108) in the TB alone group, TB/HIV co-infected group and overall proven TB group, respectively. Use of the assay devices of the present invention together with either one of the current tests could give improved sensitivities with any of the described test groups. For example, combination of the ASSURE™ TB Rapid Test with the smear test was found to have detection rates of 83% (34/41), 63% (42/67) and 70% (76/108) with the above-described test groups, respectively, whereas, a combination of the Rapid Test device with the culture test detected 81% (33/41), 70% (47/67) and 74% (80/108) of the respective test groups (Table 8).

TABLE 8

Performance of current methods and Assure ™ TB Rapid Test alone or in combinations in detecting tuberculosis patients with or without HIV co-infection

| Method | TB⁺HIV⁻ patients (n = 41) | TB⁺HIV⁺ patients (n = 67) | TB⁺ patients in total (n = 108) |
|---|---|---|---|
| AFB | 24/41 (59%) | 24/67 (36%) | 48/108 (44%) |
| Culture | 23/41 (56%) | 34/67 (55%) | 57/108 (53%) |
| Rapid Test | 29/41 (71%) | 28/67 (42%) | 57/108 (53%) |
| AFB/Culture | 26/41 (63%) | 37/67 (55%) | 62/108 (57%) |
| Rapid/AFB | 34/41 (83%) | 42/67 (63%) | 76/108 (70%) |
| Rapid/Culture | 33/41 (81%) | 47/67 (70%) | 80/108 (74%) |

The kappa statistic was used to measure the strength of agreement between the results generated by the ASSURE™ TB Rapid Test and the current approach (a combination of several methods including AFB, culture and chest X-ray). A kappa statistic value of >0.75 represents excellent agreement, while values of 0.40 to 0.75 and <0.40 represent good to fair agreement and poor agreement, respectively (Pottumarthy et al. (1999) J. Clin. Microbiol. 37(10): 3229–3232). When compared with the currently-available testing methodologies, using 96 samples from non-HIV infected patients, the agreement between the novel assay devices of the present invention and the current approaches were 71% in both of the TB positive and negative populations, with a kappa statistic of 0.41 (Table 9).

TABLE 9

Agreement between ASSURE ™ TB Rapid Test and a combination of current methods in tuberculosis patients without HIV co-infection

| TB diagnosis with current methods[a] | Rapid Test | | Agreement (%) | Kappa statistic[b] |
|---|---|---|---|---|
| | Positive | Negative | | |
| Positive | 29 | 12 | 71 | 0.41 |
| Negative | 16 | 39 | 71 | |

[a]The methods include AFB microscopy, culture and symptom diagnosis, abnormal chest X-ray.
[b]A kappa statistic of ≧0.75 represents excellent agreement, 0.40 to 0.75 represents good to fair agreement, and <0.40 represents poor agreement (Pottumarthy et al)

The above described assay devices can be packaged and sold as kits for detection of analytes. Indeed, the above devices, being self-contained and convenient for use, are themselves kits. Other kit elements can include containers for packaging one or more device elements, instruction sets for directing a user in the use of the device, i.e., according to the methods set forth herein, packaging materials, aqueous solutions for use with the device, and the like.

While the foregoing invention has been described in some detail for purposes of clarity and understanding, it will be clear to one skilled in the art from a reading of this disclosure that various changes in form and detail can be made without departing from the true scope of the present invention. For example, all the techniques, methods, compositions, apparatus and systems described above may be used in various combinations. All publications and patent documents cited in this application are incorporated by reference in their entirety for all purposes to the same extent as if each individual publication or patent, patent application, and/or other document were individually indicated to be incorporated by reference for all purposes.

What is claimed is:

1. An assay device or kit for detecting antibodies to a Mycobacterium tuberculosis antigen in a sample comprising:
   a) a chromatographic element comprising a sample receiving end, a reagent releasing end, and a reaction zone, wherein the reaction zone comprises one or more immobilized tuberculosis antigens and the reagent releasing end comprises a labeled releasable binding partner;
   b) an absorbent pad adjacent to the reaction zone; and
   c) a remobable separator positioned between the chromatraphic element and the absorbent pad, wherein the separator comprises a fluid-impermeable barrier.

2. The assay device or kit of claim 1, wherein the releasable binding partner comprises one or more antibodies directed against one or more conserved regions of a human antibody.

3. The assay device or kit of claim 1, wherein the one or more immobilized tuberculosis antigens are selected from the group consisting of CFP-10, Mtb81, DPPD, A60, LAM, ESTAT-6, 24 kDa antigen, 30-kDa antigen/85B, and 38 kDa PhoS; and wherein the labeled releasable binding partner comprises goat anti-human IgG antibodies labeled with colloidal gold.

4. The assay device or kit of claim 1, wherein the removable separator protrudes beyond the chromatographic element and the absorbent pad.

5. The assay device or kit of claim 1, wherein the removable separator is configured for removal from between the reaction zone of the chromatographic element and the absorbent pad without detachment of the removable separator from the assay device or kit.

* * * * *